United States Patent [19]
Kono et al.

[11] Patent Number: 5,562,983
[45] Date of Patent: Oct. 8, 1996

[54] ADHESIVE CLOSURE SYSTEM FOR OIL-CONTAINING SHEET MATERIAL

[75] Inventors: Yasuhiro Kono; Yorinobu Takamatsu; Kengo Imamura, all of Sagamihara, Japan

[73] Assignee: Minnesota Mining and Manufacturing Company, St. Paul, Minn.

[21] Appl. No.: 354,519

[22] Filed: Dec. 13, 1994

[51] Int. Cl.$^6$ ............................... B32B 7/12; A61F 13/15
[52] U.S. Cl. .......................... 428/355; 428/343; 604/389; 604/387
[58] Field of Search .................................. 428/355, 343; 604/389, 387; 524/127; 525/223

[56] References Cited

U.S. PATENT DOCUMENTS

| | | | |
|---|---|---|---|
| 3,691,140 | 9/1972 | Silver | 260/785 |
| 4,100,238 | 7/1978 | Shinomura | 264/49 |
| 4,166,152 | 8/1979 | Baker et al. | 428/522 |
| 4,247,498 | 1/1981 | Castro | 264/41 |
| 4,539,256 | 9/1985 | Shipman | 428/315.5 |
| 4,609,584 | 9/1986 | Cutler et al. | 428/156 |
| 4,636,432 | 1/1987 | Shibano et al. | 428/327 |
| 4,726,989 | 2/1988 | Mrozinski | 428/315.5 |
| 4,824,718 | 4/1989 | Hwang | 428/284 |
| 4,902,553 | 2/1990 | Hwang et al. | 428/156 |
| 5,125,995 | 6/1992 | D'Haese et al. | 604/389 X |
| 5,372,865 | 12/1994 | Arakawa et al. | 604/389 X |
| 5,378,405 | 1/1995 | Gutman et al. | 428/355 X |
| 5,378,536 | 1/1995 | Miller et al. | 604/389 X |
| 5,389,438 | 2/1995 | Miller et al. | 428/355 |
| 5,397,614 | 3/1995 | Patnode et al. | 428/355 X |
| 5,468,237 | 11/1995 | Miller et al. | 428/355 X |

*Primary Examiner*—Daniel Zirker
*Attorney, Agent, or Firm*—Gary L. Griswold; Walter N. Kirn; William J. Bond

[57] ABSTRACT

There is provided a disposable garment, such as a diaper, with a liquid additive, such as oil, containing microporous film and a pressure-sensitive adhesive fastening tab for releasably fastening to the microporous film. The pressure-sensitive adhesive comprises a copolymer of a) monoolefinically unsaturated monomer having an aldehyde group or ketone group and b) a base monomer.

22 Claims, 1 Drawing Sheet

ADHESIVE CLOSURE SYSTEM FOR OIL-CONTAINING SHEET MATERIAL

BACKGROUND AND FIELD OF THE INVENTION

The present invention relates to a disposable garment with an oil-containing porous sheet material.

PCT Application No. WO 94/06387 disclosed a disposable garment where oil-contamination of the adhesion surface is counteracted by using a porous web, preferably a porous film containing oil is provided, in accordance with U.S. Pat. Nos. 4,539,256; 4,726,989; 4,824,718; or 4,902,553. The oil-containing porous film can be adhered to by conventional types of rubber-resin and polyacrylate adhesives, both when contaminated by oil and when not contaminated by oil, to provide a secure closure. The preferred adhesives for use with the oil-containing porous films are described as tackified ABA type block copolymer adhesives with a certain proportion of the block copolymers having terminal B blocks. The B blocks are preferably polyisoprene and the block copolymers with terminal B blocks are SI diblock copolymers (S being polystyrene). These preferred adhesives displayed levels of adhesion suitable for forming a secure closure which adhesive tapes did not tear the oil-containing porous film when removed. However, when the oil-containing porous film is used as the disposable garment backsheet, it remains difficult to formulate an adhesive which will adequately adhere over an extended period of time without detackifying the adhesive or without excessive adhesion build-up that causes the film to tear when the adhesive tape is removed. This balance is particularly difficult when the film caliper is less than 1.5 mils (38 μ).

There continues to be a need for adhesives which can meet the unique balance of adhesive properties required to function as a disposable garment tape tab adhesive on a diaper provided with an oil-containing porous film as the disposable garment backsheet.

BRIEF DESCRIPTION OF THE INVENTION

The present invention provides a disposable garment comprising an adhesive fastening tape tab permanently adhered to one corner of the garment at a first end of the tape tab. A second free end of the adhesive fastening tape tab is provided to adhere to a outer surface of the garment to effect closure of the garment by connecting the first-mentioned corner to the outer surface by the two adhered ends of the fastening tape tab. The outer surface comprises a microporous film or web wherein the pores contain at least a minor proportion of an incompatible oil or liquid polymer, the porous outer layer provides oil-contamination tolerance, breathability and a resealable closure system with the invention pressure-sensitive adhesive fastening tape tab.

The invention pressure-sensitive adhesive fastening tape tab adhesive comprises an emulsion or suspension copolymer (A) of at least components (1) a mono-olefinically unsaturated monomer having an aldehyde group or a ketone group (sometimes referred to herein as the carbonyl monomer), and (2) a base monomer; crosslinked with a polyfunctional hydrazide (B).

The mono-olefinic unsaturation in the carbonyl monomer may be provided by (meth)acrylate, (meth)acrylamide or styryl functionality. Examples of suitable carbonyl monomers include acrolein, vinyl methyl ketone, vinyl ethyl ketone, vinyl isobutyl ketone, diacetone (meth)acrylamide, formylstyrol, diacetone (meth)acrylate, acetonyl acrylate, 2-hydroxypropyl acrylate-acetyl acetate, 1,4-butanediol acrylate acetylacetate, and mixtures thereof.

Preferably, the base monomer is an alkyl (meth) acrylate ester, a vinyl ester, or mixtures thereof. More preferred base monomers are monofunctional unsaturated (meth) acrylate esters of non-tertiary alkyl alcohols, the alkyl groups of which have from 4 to 14 carbon atoms (most preferably from 4 to 10 carbon atoms).

The adhesive copolymer may optionally include a polar monomer that is copolymerizable with the carbonyl monomer and the base monomer. The adhesive copolymer further include a multifunctional free-radically polymerizable crosslinking agent for internally crosslinking the copolymer.

Advantageously, it has been found that by adding a polyhydrazide (i.e., a material containing more than one hydrazino moiety) to the adhesive copolymer, a pressure-sensitive adhesive having moderate peel and excellent shear strength to the microporous film, reduced adhesive transfer, improved aqueous or polar solvent resistance (as measured by the indispersibility of the adhesive in solvent) can be provided, which has a stable pot life for improved processability and is environmentally advantageous as it can be applied out of an aqueous solvent rather than an organic solvent. It is believed that the polyhydrazide externally (i.e., interpartically) crosslinks the adhesive copolymer together.

Useful polyhydrazides have the general structure:

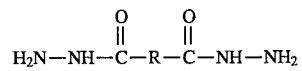

wherein R is an organic radical containing about 2 to 10 carbon atoms. Examples of suitable polyhydrazides include oxalyl dihydrazide, malonyl dihydrazide, succinyl dihydrazide, glutaryl dihydrazide, adipoyl dihydrazide, maleyl dihydrazide, sebacoyl dihydrazide, fumaroyl dihydrazide, isophthalic diydrazide, terephthalic dihydrazide, and mixtures thereof.

In preferred embodiments, the pressure sensitive adhesives comprise:

(a) pressure sensitive adhesive copolymers that are the polymerization product of:

(1) about 75 to 99.9 parts by weight (more preferably about 80 to 99 parts, most preferably about 85 to 98 parts) of a free-radically polymerizable monomer selected from the group consisting of alkyl (meth)acrylate esters, vinyl esters, and mixtures thereof;

(2) about 0.1 to 10 parts by weight (more preferably about 0.5 to 7 parts, most preferably about 1 to 5 parts) of a mono-olefinically unsaturated monomer having an aldehyde group or a ketone group; and (3) optionally, 0 to about 20 parts by weight (more preferably 0 to about 15 parts, most preferably 0 to about 10 parts) of a polar monomer different than the carbonyl monomer and the base monomer;

wherein the sum of (a) (1)+(a) (2)+(a) (3) is 100 parts by weight; and (b) about 0.5 to 150 milliequivalents (meq) per 100 grams of adhesive copolymer (more preferably about 1 to 100 meq, most preferably about 2 to 50 meq) of a polyhydrazide crosslinking agent for crosslinking the adhesive copolymers together.

A variety of different methods may be used to prepare the pressure sensitive adhesives. In general, these methods involve aqueous suspension or emulsion polymerizing the pressure sensitive adhesive copolymer, forming microparticles, and then adding to the aqueous suspension or emulsion a crosslinking agent for crosslinking the microparticles together. However, bulk, solution or dispersion polymerization can also be used. The pressure sensitive adhesive fastening tape tabs can be prepared by applying an aqueous media of copolymer and crosslinking agent to a backing to form a wet adhesive layer and then drying the wet adhesive. Once dried, the pressure sensitive adhesive copolymers are crosslinked together.

DESCRIPTION OF THE PREFERRED EMBODIMENTS

Figure 1:
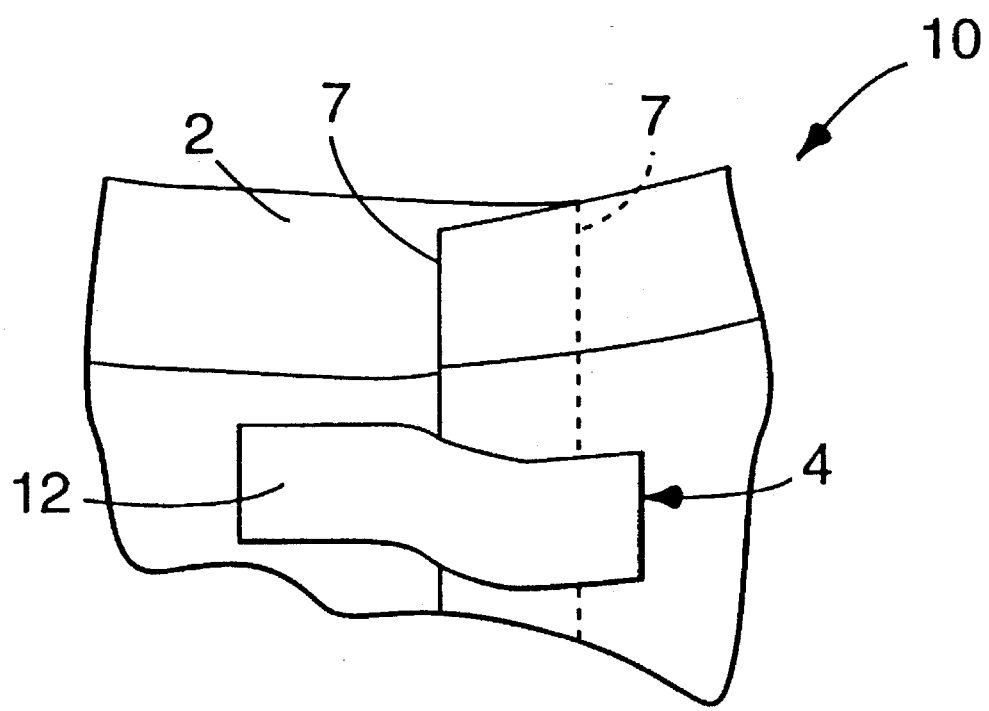
FIG. 1 is a cutaway view of the invention closure system.

The microporous film, resealable adhesive closure system will be described with reference to a conventional closure system which could be used in applications requiring a microporous film and using adhesive fastening tabs, such as disposable incontinent garments, disposable medical gowns, caps, packaging systems, feminine hygiene articles, and the like.

A conventional pressure-sensitive adhesive closure system 10 as used on a disposable garment is depicted in FIG. 1. The disposable garment is provided with a thin liquid-impermeable outer microporous film 2. Adhesive fastening tape tabs 4 are provided at one opposed side edge region 7 with a free end 12 of the fastening tab 4 removably attached to an opposing edge region 7. The oil-containing microporous film exhibits the ability to provide a suitable surface for adhering to the invention fastening tab free end 12 under normal use conditions, and when contaminated with externally applied oil. Prior to use, the adhesive surface on the free end 12 of the adhesive fastening tape tab 4 can be protected from contamination by a release-coated paper or a release-coated tape, which can be provided on the opposite face of the corners 7. However, the preferred invention adhesives can generally be used without a release tape.

The oil-containing microporous film (one having an effective pore size of about 10 microns or less, preferably less than 1 micron) is preferably a film such as is disclosed in U.S. Pat. Nos. 4,902,553; 4,539,256; 4,609,584; 4,726,989 or 4,824,718. The material described in these patents comprises a microporous film formed by dissolving a crystallizable polymeric material in a liquid additive at a temperature above the melt temperature of the polymeric material and forming this melt forming this melt into a film, such as by extrusion. The homogeneous solution is then permitted to cool at a rate suitable to cause the crystallizable polymer to crystallize into a distinct interconnected phase, the polymer being incompatible with the additive at ambient or use conditions. The phase-distinct film material is then uniaxially or multiaxially orientated, creating a film with micropores, which pores contain the phase- distinct liquid additive. The liquid additive is preferably one which exhibits plasticizing properties or affinity to the adhesive on the free end of the fastening tab. Potential additive materials include saturated hydrocarbons such as mineral oil, glycerin, petroleum jelly, low molecular weight polyethylene, polyethylene oxide, polypropylene oxide, polytetramethylene oxide, soft carbowax, plasticizing oils, and the like. Preferred additive materials are plasticizing oils, with mineral oil being particularly preferred because of its relatively low cost and excellent film-forming properties. The crystallizable polymeric material is preferably olefinic, such as polyolefins, or condensation polymers such as polyesters or polyamides. Most preferred are polyolefins such as crystalline isotactic polypropylene, polyethylene, polybutylene, polyethylpentene, copolymers, block polymers and modified versions thereof.

The additive liquid can be used in an amount ranging from about 5 to 80 percent by weight of the formed film, preferably 5 to 50 percent, and most preferably 10 to 30 percent.

Discussions of crystallizable polymers and phase-separating additives are also found in U.S. Pat. No. 4,247,498 and U.S. Pat. No. 4,100,238. For example, for isotactic polypropylene, these patents describe, the use of phase-separable additives such as poly-1-butene, polyethylene wax, low molecular weight polyethylene, alcohols, aldehydes, amines, esters such as methylene benzoate, ethers such as diphenylether, hydrocarbons such as trans-stilbene or ketones.

Nucleating agents such as those described in U.S. Pat. No. 4,824,718 and U.S. Pat. No. 4,726,989 can also be used to produce uniform crystallization of the polymeric material upon cooling. These nucleating agents preferably are at least a primary agent, generally an organic acid or derivative, which dissolves in the liquid additive at a temperature at least more than 10° C. above the crystalline transition temperature of the thermoplastic polymer, and which is used in amounts from 0.05 to 5 percent by weight of the system, and optionally a secondary inert nucleating agent, which is employed in approximately the same concentration. The secondary inert nucleating agent normally comprises an inorganic particulate material such as talc, titanium dioxide, calcium carbonate, magnesium carbonate, barium carbonate, magnesium sulfide, barium sulfide, and the like. Suitable organic acids include mono- or polyacids, e.g., carboxylic acids, sulfonic acids, phosphoric acids, and solid organic alcohols such as dibenzylidene sorbitol. The preferred organic acids include adipic acid and succinic acid, and a preferred secondary nucleating agent is talc.

Following precipitation of the thermoplastic crystallizable polymer, the film can be used unoriented or preferably orientated with a stretch ratio, in at least one direction, of 0 to 3, preferably from 1.5 to 2.5. When the film is not oriented, the liquid additive is preferably washed from the film.

Generally, the thickness of the microporous reinforcement sheet is from 5 to 250 microns, preferably from 10 to 150 microns. Comparatively, thinner films are preferred in terms of cost and increased moisture vapor permeability where employed for this additional purpose. However, too thin a film may be inadequate in providing a disposable garment backsheet sufficiently resistant to tearing. Thicker films provide improved tensile performance and reinforcement against more aggressive adhesives, however, at significantly greater cost.

The fastening tape tab 4 adhesives are based on polymeric pressure-sensitive adhesive copolymers. The preferred microparticles, and other adhesive copolymers, comprise and, more preferably consist essentially of, the polymerization product of: (a) a mono-olefinically unsaturated monomer that contains an aldehyde moiety or a ketone moiety (sometimes referred to herein as the "carbonyl monomer") and (b) a second or base monomer. In particularly preferred embodiments of the invention, the pressure-sensitive adhesives further include a polyhydrazide. As explained in more detail below, it is believed that the polyhydrazide reacts with the carbonyl group on the carbonyl monomer to externally or interpartically crosslink the adhesive copolymer together, thereby enhancing the shear strength to the microporous film and solvent resistance of the pressure sensitive adhesive while reducing the amount of adhesive transfer and improving processability and environmental friendliness.

Turning now to the specific components of the adhesive, the carbonyl monomer preferably has the following general structure:

wherein R is an organic radical that is bonded to the carbonyl carbon atom by another carbon atom and contains a single, free-radically polymerizable carbon atom-to-carbon atom double bond. The mono-olefinic unsaturation may be provided by (meth)acrylate, (meth) acrylamide, styryl or other vinyl functionalities. Preferably it is provided by acrylate or acrylamide functionality. (The use of the term "meth" in parentheses indicates that, for example, both acrylate and methacrylate groups are contemplated.) $R^1$ is hydrogen or an organic radical that is bonded to the carbonyl carbon atom by another carbon atom. Both R and $R^1$ may contain any number of carbon atoms, may be aliphatic or aromatic, may be branched or linear, and may contain other functionalities such as ester or amide groups.

Examples of useful carbonyl monomers include acrolein, vinyl methyl ketone, vinyl ethyl ketone, vinyl isobutyl ketone, diacetone (meth)acrylamide, formylstyrol, diacetone (meth)acrylate, acetonyl acrylate, 2-hydroxypropyl acrylate-acetyl acetate, 1,4-butanediol acrylate acetylacetate, and mixtures thereof. Acrolein and diacetone acrylamide are particularly preferred.

In order to accommodate the preferred suspension polymerization manufacturing process for the adhesive microparticles (discussed below), the carbonyl monomer has at least some oil solubility, although it is preferred that it be both somewhat oil soluble and water soluble.

The carbonyl monomer is employed in an amount sufficient to provide good crosslinking of the copolymer, including the preferred microparticles, upon reaction with the polyhydrazide.

The carbonyl monomer is typically used in an amount of about 0.1 to 10 parts by weight. If the carbonyl monomer provides less than about 0.1 part by weight, then the level of interparticle crosslinking tends to be insufficient resulting in adhesives having poor cohesive strength, low shear strength, and increased adhesive transfer. If the carbonyl monomer provides more than about 10 parts by weight, then the resulting polymer tends to be non-tacky and loses pressure sensitive adhesive properties, due to an increased storage modules.

The base monomer is polymerizable with the carbonyl monomer, preferably free-radically polymerizable. The base monomers are oleophilic, water emulsifiable, and have limited water solubility so as to permit the formation of a stable suspension polymerizable system for manufacture of the preferred adhesive microparticles and other adhesive copolymers. As homopolymers, base monomers generally have glass transition temperatures below about −10° C. to facilitate the provision of pressure sensitive adhesive properties.

Alkyl (meth)acrylate monomers may be used to provide the base monomer. Particularly preferred are monofunctional unsaturated (meth)acrylate esters of non-tertiary alkyl alcohols. The alkyl groups of these alcohols preferably contain from 4 to 14 (more preferably 4 to 10) carbon atoms. (Meth)acrylate esters prepared from alkyl alcohols having less than 4 or more than 14 carbon atoms tend to have inadequate pressure sensitive adhesive properties.

Examples of useful monomers include sec-butyl acrylate, n-butyl acrylate, isoamyl acrylate, 2-methylbutyl acrylate, 4-methyl- 2-pentyl acrylate, 2-ethylhexyl acrylate, isooctyl acrylate, isononyl acrylate, isodecyl methacrylate, isodecyl acrylate, dodecyl acrylate, tetradecyl acrylate, and mixtures thereof. Particularly preferred are n-butyl acrylate, secbutyl acrylate, isoamyl acrylate, 2-ethylhexyl acrylate, isooctyl acrylate, isononyl acrylate, isodecyl acrylate, and mixtures thereof. Of these, isooctyl acrylate and 2-ethylhexyl acrylate are the most preferred.

Also useful for providing the base monomer are mono-functional, unsaturated vinyl esters derived from linear or branched carboxylic acids having 1 to 14 (preferably 7 to 12) carbon atoms (not counting the carboxyl carbon atom). Suitable vinyl ester monomers include vinyl propionate, vinyl pelargonate, vinyl hexanoate, vinyl caprate, vinyl 2-ethylhexanoate, vinyl octanoate, vinyl decanoate, vinyl laurate, and mixtures thereof. Particularly preferred are vinyl caprate, vinyl 2-ethylhexanoate, vinyl laurate, and mixtures thereof.

(Meth)acrylate or other vinyl monomers which, as homopolymers, have glass transition temperatures higher than about −20° to 0° C., e.g., ethyl acrylate, tert-butyl acrylate, isobornyl acrylate, butyl methacrylate, vinyl acetate, acrylonitrile, mixtures thereof, and the like, may be used in conjunction with one or more of the (meth)acrylate and vinyl ester monomers provided that the glass transition temperature of the resulting polymer is below about −10° C., preferably below −20° C., and has pressure sensitive adhesive properties.

Advantageously, the pressure sensitive adhesive copolymers of the invention may be prepared without polar monomers. That is, the copolymers may be prepared using: alkyl (meth)acrylate and/or vinyl ester base monomer(s), alone or in combination only with other free-radically polymerizable vinyl functional base monomers; and carbonyl monomers. Polar monomers can render the resulting adhesive more sensitive to moisture (e.g., loss of adhesion in high humidity environments). However, polar monomers may be beneficial in some instances. Consequently, the pressure sensitive adhesives of the invention may further and optionally comprise a polar monomer different than but copolymerizable with the carbonyl monomer and the base monomer. The polar monomer may be added to improve or modify cohesive strength, storage stability, adhesion to polar surfaces, and glass transition temperature. It is preferred that the polar monomer be incorporated in an amount of no more than about 1 to 20 parts by weight, if it is used at all. Polar monomers refer to monomers that are both oil and water soluble, are polymerizable with but different than the carbonyl monomer and the base monomer.

The pressure sensitive adhesive copolymers of the invention preferably comprise: (a) about 0.1 to 10 parts by weight carbonyl monomer; (b) about 75 to 99.9 parts by weight base monomer; and, optionally, (c) 0 to about 20 parts by weight polar monomer. More preferably, the pressure sensitive adhesive copolymers comprise: (a) about 0.5 to 7.0 parts by weight carbonyl monomer; (b) about 80 to 99 parts by weight base monomer; and, optionally, (c) 0 to about 15 parts by weight polar monomer. Most preferably, the pressure sensitive adhesive copolymers comprise: (a) about 1.0 to 5.0 parts by weight carbonyl monomer; (b) about 85 to 98 parts by weight base monomer, and, optionally, (c) 0 to about 10 parts by weight polar monomer. The parts by weight ranges are based on the sum of (a)+(b)+(c) nominally equalling 100 parts.

The pressure sensitive adhesive copolymers of the invention may also contain a multifunctional free-radically polymerizable crosslinking agent. Such crosslinking agents can enhance the cohesive strength and solvent insolubility of the individual microparticles by internally crosslinking them. "Multifunctional" refers to crosslinking agents which possess two or more free-radically polymerizable olefinically unsaturated groups. Useful multifunctional crosslinking agents include (meth)acrylic esters of diols (e.g., butanediol), triols (e.g., glycerol), and tetrols (e.g., pentaerythritol); polymeric multifunctional (meth)acrylates (e.g., poly(ethylene oxide) diacrylate and poly(ethylene oxide) dimethacrylate); polyvinylic compounds (e.g., substituted and unsubstituted divinylbenzene); difunctional urethane acrylates; and mixtures thereof.

When an internal crosslinking agent is employed, it is typically used at a level of up to about 0.15 equivalent weight percent. Above about 0.15 equivalent weight percent, the microparticles tend to lose their pressure sensitive adhesive qualities and eventually become non-tacky to the touch at room temperature. The "equivalent weight percent" of a given compound is defined as the number of equivalents of that compound divided by the total number of equivalents of free-radically polymerizable unsaturation in the total microparticle composition. An equivalent is the number of grams divided by the equivalent weight. The equivalent weight is defined as the molecular weight divided by the number of polymerizable groups in the monomer (in the case of those monomers with only one polymerizable group, equivalent weight=molecular weight).

A polyfunctional hydrazide (sometimes described herein as a polyhydrazide) refers to a compound having more than one hydrazino moiety; i.e, more than one —NH—NH$_2$ moiety. Polyhydrazides are typically obtained as the reaction product of hydrazine and a polyfunctional organic carboxylic acid (or its corresponding ester, amide, acyl halide or anhydride). The polyfunctional organic carboxylic acid may be aliphatic or aromatic in nature and may contain a branched or linear backbone. Preferably, the acid is a dicarboxylic acid so as to result in a polyhydrazide having the following general structure:

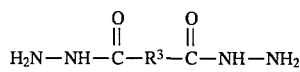

wherein R$^3$ is an organic radical containing about 2 to 10 carbon atoms. As the molecular weight and size of the R$^3$ group increases, the solubility of the polyhydrazide in water declines.

The polyhydrazide may also be provided by a poly(acrylhydrazide) which is typically obtained by reacting a polymer of a polyfunctional organic carboxylic acid (or its corresponding ester, amide, acyl halide or anhydride) with hydrazine. Also useful are bis-semicarbazides, especially those which are aliphatic or cycloaliphatic and have the following general structure:

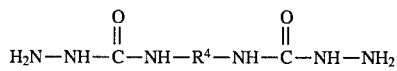

wherein R$^4$ is a straight chain or branched radical having 2 to 7 carbon atoms or a cycloaliphatic radical having 6 to 8 carbon atoms.

Examples of useful polyhydrazides include oxalyl dihydrazide, malonyl dihydrazide, succinyl dihydrazide, glutaryl dihydrazide, adipoyl dihydrazide, maleyl dihydrazide, sebacoyl dihydrazide, fumaroyl dihydrazide, isophthalic dihydrazide, terephthalic dihydrazide, and mixtures thereof. Particularly preferred polyhydrazides include malonyl dihydrazide and adipoyl dihydrazide.

Broadly, the polyhydrazide is used in an amount of about 0.5 to 150 milliequivalents (meq) per 100 grams of pressure sensitive adhesive copolymer (the copolymer being the polymerization product of the carbonyl monomer, the base monomer, and any optional polar monomer). The number of milliequivalents is equal to the number of equivalents of hydrazine functionality multiplied by 1000, and the number of equivalents is the multiplication product of the number of moles of polyhydrazide and the functionality of the polyhydrazide. If the amount of polyhydrazide is less than about 0.5 meq, then the level of interparticle crosslinking is reduced and the pressure sensitive adhesive copolymers exhibit lower shear strength and have a higher tendency toward adhesive transfer. If the amount of polyhydrazide is greater than about 150 meq, then the copolymers are more highly crosslinked and show less pressure sensitive adhesive properties. More preferred is to use about 1 to 100 meq of the polyhydrazide. Most preferred is a level of about 2 to 50 meq.

The pressure sensitive adhesive copolymers of the invention may be prepared by a variety of different methods, however, preferred are suspension or emulsion polymerization of microparticles. The resulting microparticles tend to be bead or pearl shaped, although they may more spheroidal. Typically, they have an average diameter of about 1 to 300 μm (more preferably, about 1 to 50 μm) for suspension polymerization and 0.1 to 1 microns for emulsion polymerization. The microparticles may be solid, or hollow if made by suspension polymerization.

Solid pressure sensitive adhesive microparticles may be prepared via the suspension polymerizations disclosed in U.S. Pat. Nos. 3,691,140; 4,166,152; and 4,636,432. In general, these suspension polymerization techniques use ionic or nonionic emulsifiers in an amount greater than the critical micelle concentration and/or protective colloids, finely divided inorganic solids, or the like. The microparticles can generally have a particle size of 1–300 microns. This method allows one to reduce the amount of surfactant in the adhesive copolymer increasing the moisture resistance of the adhesive copolymer.

Generally the adhesive copolymer has a glass transition temperature (Tg) of from −80° to −20° C. This range of Tg values is advantageous in terms of preferred peel and shear adhesion to the microporous film. With a copolymer having a Tg greater than −20° C. the adhesive on the disposable garment fastening tape tab can tear the microporous film when the tape tab is removed from the microporous film, with a copolymer having a Tg of less than −80° C. the adhesive loses tack. Preferably, the copolymer Tg is in the range of −60° to −30° C. and most preferably −55° to −45° C. The Tg is determined by known methods using a differential scanning colorimeter.

Each suspension polymerization method (whether producing hollow or solid microparticles) may be modified by withholding the addition of all or some of the carbonyl monomer and/or any optional polar monomer until after polymerization of the oil phase base monomer has been initiated. In this instance, however, these components must be added to the polymerizing mixture prior to 100% conversion of the base monomer. Similarly, the internal crosslinker (if used) can be added at any time before 100% conversion to polymer of the monomers of the microparticle composition. Preferably it is added before initiation occurs.

Once the pressure sensitive adhesive copolymers have been polymerized, but while they are dispersed in the aqueous media (with bulk, solution or like polymerization the polymers are later dispersed in an aqueous media), the polyhydrazide may be added either as an aqueous solution or as a solid powder that dissolves in the aqueous media.

Other ingredients which may be optionally added to the adhesive copolymer aqueous media following polymerization include tackifying resins, plasticizers, pigments, neutralizing agents (e.g., sodium hydroxide), fillers, stabilizers, and various polymeric additives. These ingredients are incorporated in amounts that do not materially adversely affect the desired properties of the pressure sensitive adhesive copolymers.

If the copolymers were prepared without polyhydrazide, then the aqueous media of copolymers may be sprayed by conventional techniques without cobwebbing, or they may be sprayed from an aerosol container with suitable propellants such as alkanes, alkenes, and chlorofluorocarbons (e.g., Freon™ halocarbons from E.I. dupont de Nemours & Co., Inc.). Useful aerosols preferably have a solids content of about 5% to 20%, more preferably about 10% to 16%.

The aqueous media may also be coated onto an appropriate substrate and dried. Drying may be accomplished under ambient conditions or, more quickly, by heating for about 2 to 20 minutes in a 60° to 120° C. oven, the actual time and temperature depending on the substrate (For systems containing a poly(acylhydrazide) external crosslinker, heated drying is required.).

An aqueous suspension of pressure sensitive adhesive microparticles may be dried and then redispersed (with agitation if necessary) in common organic liquid solvents such as ethyl acetate, tetrahydrofuran, heptane, 2-butanone, benzene, and cyclohexane. The solvent dispersions may be sprayed or they may be coated onto a suitable backing and dried. However, once the microparticles have been dried, they cannot be redispersed in water.

If pressure sensitive adhesive copolymers have been prepared with polyhydrazide, then the aqueous media of adhesive copolymer may be sprayed by conventional techniques without cobwebbing or they may be sprayed from an aerosol container, as describe above. In addition, the aqueous media may be coated onto an appropriate substrate and dried, as described above. However, once these copolymers have been dried, they can no longer be redispersed, either in water or common organic liquid solvents. Thus, the dried pressure-sensitive adhesive copolymers that include polyhydrazide may be regarded as solvent indispersible.

While not wishing to be bound by any particular theory, it is believed that the polyhydrazide is essentially unreactive toward the copolymers in the aqueous media. However, as the water is removed from the aqueous media upon drying, a dehydration condensation reaction occurs between the carbonyl groups provided in the microparticles by the carbonyl monomer and the hydrazino moieties. In preferred systems, this reaction proceeds at a high rate under ambient conditions and forms covalent linkages between microparticles. In this way, the pressure-sensitive adhesive copolymers may be regarded as interpartically or externally crosslinked.

The inert nature of the polyhydrazide when in suspension, coupled with its ability to rapidly form interparticle covalent crosslinks between copolymers when the water is removed, offers a number of important advantages, as explained below.

As noted above, the pressure sensitive adhesive copolymers of the invention may be coated onto a suitable substrate, generally at a coating weight of 5 to 80 g/m². Useful substrates include paper, plastic films, cellulose acetate, ethyl cellulose, woven or nonwoven fabric formed of synthetic or natural materials, metal, metallized plastic films, and ceramic sheets. Coating can be accomplished with a knife coater, Meyer bar coater, or an extrusion die. In this manner, a wide variety of useful articles may be provided.

The present invention will be further described with reference to working examples and comparative examples thereof. Note, however, that the present invention is not restricted by these examples.

EXAMPLES 1 TO 13

These examples are intended to evidence the composition of different adhesives and its effects on properties of the resulting adhesive tapes. Note that Examples 11 and 12 are comparative examples.

Preparation of Adhesive Tapes

Using the following monomers, the thirteen (13) adhesives tapes were prepared:
2-ethylhexyl acrylate (2-EHA);
isooctyl acrylate (IOA);
acrylic acid (AA);
isononyl acrylate (INA);
n-butyl acrylate (BA);
vinyl acetate (VAc);
ethyl acrylate (EA);
lauryl methacrylate (LMA);
diacetone acrylamide (DAACM); and
acrolein (Ac).

Adipolyl dihydrazide (ADH) or malonyl dihydrazide (MDH) was used as a crosslinking agent.

A. Emulsion Polymerization:

The monomer(s) described in the following Table 1 were weighed to obtain the described amount, and mixed with water in an amount of 138 parts by weight per 100 parts by weight of the monomer(s). The mixture was admixed with 2 parts by weight of sodium dodecyl sulfate as an emulsifier. After addition of 0.2 parts by weight of ammonium persulfate as a polymerization initiator, the monomer(s) were polymerized at 60° C for three (3) hours in an atmosphere of nitrogen gas. An aqueous emulsion of the polymer was thus obtained.

B. Suspension Polymerization:

The procedure of the emulsion polymerization (A) was repeated except that one percent of sodium poly(oxyethylene) nonylphenylether sulfate (Levenol™ commercially available from Kao Corporation) was used in place of sodium dodecyl sulfate as an emulsifier, 0.2 percent of azobis-2,4-dimethylvaleronitrile (AVN) was used in place of ammonium persulfate as a polymerization initiator, and the monomer(s) were polymerized at 40° C. for 24 hours.

Determination of Glass Transition Temperature, Tg (°C.):

The polymer was recovered from the obtained emulsion or suspension of polymer, and 15 mg of the polymer was used for the determination of Tg. The Tg was determined at a rate of temperature increase of 10° C./min. in an atmosphere nitrogen gas on a differential scanning calorimeter: DSC-2C commercially available from Perkin Elmer Company. The results are summarized in Table 1.

Adipoyl dihydrazide (ADH) or malonyl dihydrazide (MDH) as a crosslinking agent was then added to the aqueous emulsion or suspension of the polymer. The amount of ADH or MDH added is described in Table 1.

One surface of the polypropylene (PP) tape having a thickness of 50 microns was coated with the aqueous adhesive composition at a dry coverage of about 20 g/m² by a knife coater. The coated tape was then dried at 100° to 120° C. for three minutes in a drying oven. An adhesive tape was obtained.

Evaluation Tests of Adhesive Tapes

Each of the adhesive tapes was subjected to the following evaluation tests in accordance with the procedures as described below.

1. Adhesion Test (Initial peel strength, g/25 mm)

The adhesive tape having a width of 25 mm was applied to a single surface of a microporous oil-containing sheet (polypropylene with 30% oil) having a size of 75 mm×75 mm, and a peel strength (g/25 mm) at 180° was determined in a tensile strength tester. The test conditions are as follows:

rate of tensile pulling: 300 mm/min atmosphere: 23° C., 50 percent RH

The evaluation was made under the following criteria:

The adhesive tape can satisfy the requirements of the present invention, if it can be peeled off from the adhered without complete damaging thereof, or it does not show less peel strength of less than 200 g/25 mm. The adhesive tape is evaluated to be the most suitable, if it can be peeled off from the adhered with no damaging thereof, or shows a peel strength of 300 to 800 g/25 mm.

2. Adhesion Test (peel after aging, g/25 mm)

The procedure of Test No. 1 was repeated except that the determination was made after aging at 40° C. and 24 hours. The evaluation was made under the above-mentioned criteria of Test No. 1.

3. Holding Test (holding power, min)

The adhesive tape having a size of 25 mm×25 mm was applied to a single surface of a microporous oil-containing sheet (polypropylene with 30% oil) having a size of 75 mm×75 mm, the sheet with the adhesive tape was vertically disposed, and a vertical load was applied to the sheet. The time (minutes) until the load falls was determined under the following test conditions:

load applied: 500 g temperature of atmosphere: 40° C.

The evaluation was made under the following criteria:

The adhesive tape can satisfy the requirements of the present invention, if the holding power is 10 minutes or more. The adhesive tape is evaluated to be the most suitable, if the holding power is 60 minutes or more.

4. Tests for Releasability and Humidity Resistance

The adhesive tape having a width of 25 mm was applied to a single surface of the porous oil-containing sheet (polypropylene with 30% oil) having a size of 75 mm×75 mm, and the sheet with the adhesive tape was left to stand at 50° C. and 95% RH for 5 hours. The tape was then peeled off from the sheet, and the surface of the sheet was visually observed in order to ascertain whether a residue of the adhesive appears on the surface of the sheet.

The evaluation was made under the following criteria:

Good: No residue;

Fair: A little residue; and

Bad: Not acceptable residue.

The results of these tests are summarized in the following Table 1. The results of this table evidences that according to the present invention, excellent adhesive tapes and excellent articles made therewith can be provided.

TABLE 1

| Example No. | Composition of Starting Materials | | | | | | No. of Test | | | | Type of polymer- ization | Ave. size of particles ($\mu$m) |
| | Monomer (100 pbW) | DAACM (pbw) | Ac (pbw) | ADH (meq)* | MDH (meq)* | Tg (°C.) | 1 | 2 | 3 | 4 | | |
| --- | --- | --- | --- | --- | --- | --- | --- | --- | --- | --- | --- | --- |
| 1 | 2 EHA | 0.1 | | 2.9 | | −65 | 520 | 795 | 40 | Fair | Emul. | 0.3 |
| 2 | 2 EHA | 1 | | 2.9 | | −63 | 515 | 792 | 53 | Good | Emul. | 0.3 |
| 3 | 2 EHA | 3 | | 2.9 | | −60 | 400 | 790 | 55 | Good | Emul. | 0.3 |
| 4 | 2 EHA (95/5) | 5 | | 2.9 | | −50 | 465 | 765 | 101 | Good | Emul. | 0.3 |
| 5 | IOA | 7 | | 2.9 | | −38 | 140 | 180 | 35 | Good | Emul. | 0.3 |
| 6 | INA | | 1 | 2.9 | | −63 | 420 | 700 | 45 | Good | Emul. | 0.3 |
| 7 | 2 EHA/BA (90/10) | 1 | | 2.9 | | −61 | 480 | 720 | 30 | Good | Emul. | 0.3 |
| 8 | IOA/EA (95/5) | 2 | | 2.9 | | −49 | 340 | 560 | 539 | Good | Susp. | 1.6 |
| 9 | IOA/EA (95/5) | 2 | | | 7.6 | −49 | 280 | 480 | 500 | Good | Susp. | 2.5 |
| 10 | LMA | 2 | | 2.9 | | −65 | 510 | 780 | 58 | Good | Emul. | 0.3 |
| 11 | 2 EHA | | | 2.9 | | −65 | >800 | tear | 5 | Bad | Emul. | 0.3 |
| 12 | IOA/AA (95/5) | | | | | −50 | 700 | tear | 18 | Bad | Susp. | 2.0 |
| 13 | BA/VAc/AA (50/46/4) | 1 | | 2.9 | | −20 | >800 | >800 | 334 | Good | Emul. | 0.3 |

Notes:
Test No. 1: Initial peel (g/25 mm)
Test No. 2: Peel after aging (g/25 mm)
Test No. 3: Holding power (min.)
Test No. 4: Humidity resistance
*Milli-equivalents per 100 g copolymer
pbw: parts by weight
Examples Nos. 11 and 12 are comparative examples

EXAMPLES 14 TO 21

These examples are intended to evidence effects of the amount of the crosslinking agent on properties of the resulting adhesive tapes and articles made therewith. Note that Example 14 is a comparative example.

The procedure of Examples 1 to 13 were repeated except that the amount of the crosslinking agent (ADH) was changed as indicated in Table 2 and other changes were made as also indicated in Table 2. The results are summarized in the following Table 2.

TABLE 2

| Example No. | Composition of Starting Materials | | | | | No. of Test | | | | Type of polymerization | Ave. size of particles (μm) |
|---|---|---|---|---|---|---|---|---|---|---|---|
| | Monomer (100 pbw) | DAACM (pbw) | Ac (pbw) | MDH (meq)* | Tg (°C.) | 1 | 2 | 3 | 4 | | |
| 14 | IOA | 2 | | | −53 | >800 | tear | 2 | Bad | Susp. | 2.3 |
| 15 | IOA | 2 | | 0.2 | −53 | 720 | >800 | 18 | Fair | Susp. | 2.3 |
| 16 | IOA | 2 | | 0.5 | −53 | 612 | >800 | 42 | Fair | Susp. | 2.3 |
| 17 | IOA | 2 | | 2.4 | −53 | 530 | 785 | 125 | Good | Susp. | 2.3 |
| 18 | IOA | 2 | | 5.9 | −53 | 340 | 620 | >800 | Good | Susp. | 2.3 |
| 19 | IOA | 2 | | 11.8 | −53 | 330 | 495 | >800 | Good | Susp. | 2.3 |
| 20 | IOA | 2 | | 17.8 | −53 | 275 | 390 | 183 | Good | Susp. | 2.3 |
| 21 | IOA | 2 | | 23.7 | −53 | 230 | 295 | 35 | Good | Susp. | 2.3 |

Notes:
Test No. 1: Initial peel (g/25 mm)
Test No. 2: Peel after aging (g/25 mm)
Test No. 3: Holding power (min.)
Test No. 4: Humidity resistance
*Milli-equivalents per 100 grams copolymer
pbw: Parts by weight
Examples No. 14 is a comparative example.

We claim:

1. A disposable garment comprising a thin liquid-impermeable sheet material of a liquid additive containing microporous film and a closure system comprising a pressure-sensitive adhesive fastening tab having a first free end for releasably attaching to said liquid additive containing microporous film, said fastening tab permanently attached, at a second end opposite the free end, to a first edge region of the garment, said fastening tab free end having a layer of pressure-sensitive adhesive microparticles said microparticles comprising a copolymer comprising the polymerization product of a) 0.1 to 10 parts by weight of a mono-olefinically unsaturated monomer having an aldehyde group or a ketone group; b) 75 to 94 parts by weight of a free radically polymerizable base monomer selected from the group consisting of alkyl (meth)acrylate esters, vinyl esters and mixtures thereof; and c) 0 to about 20 by weight of a polar monomer different than monomers a) and b) wherein the microparticles are crosslinked together by a polyhydrazide crosslinking agent.

2. The disposable garment of claim 1 wherein the liquid additive comprises 5 to 50 percent by weight of the film, and the film is oriented.

3. The disposable garment of claim 2 wherein the liquid additive comprises 10 to 30 percent by weight of the film, and the film is oriented by up to 3.0 to 1 in at least one direction.

4. The disposable garment of claim 3 wherein the liquid additive is selected from plasticizing oil, glycerine, petroleum jelly, soft carbowax, low molecular weight polyethylene, polyethylene oxide, polypropylene oxide, polytetramethylene oxide, and mixtures thereof.

5. The disposable garment of claim 4 wherein the liquid additive is a mineral oil.

6. The disposable garment of claim 1 wherein the microparticles are suspension copolymers.

7. The disposable garment of claim 1 wherein the microparticles are emulsion copolymers.

8. The disposable garment of claim 1 wherein the pressure-sensitive adhesive copolymer has a glass transition temperature of from −80° to −20° C.

9. The disposable garment of claim 1 wherein the pressure-sensitive adhesive copolymer has a glass transition temperature of from −60° to −30° C.

10. The disposable garment of claim 1 wherein the base monomer is a monofunctional unsaturated (meth) acrylate ester of a non-tertiary alkyl alcohol, the alkyl group of which has from 4 to 14 carbon atoms.

11. The disposable garment of claim 1 wherein the mono-olefinic unsaturation in monomer (a) is provided by (meth) acrylate, (meth) acrylamide or styryl functionality.

12. The disposable garment of claim 11 wherein monomer (a) is selected from the group consisting of acrolein, vinyl methyl ketone, vinyl ethyl ketone, vinyl isobutyl ketone, diacetone (meth)acrylamide, formylstyrol, diacetone (meth)acrylate, acetonyl acrylate, 2-hydroxypropyl acrylate-acetyl acetate, 1,4-butanediol acrylate-acetyl acetate, and mixtures thereof.

13. The disposable garment of claim 1 wherein the polyhydrazide has the general structure:

wherein R is an organic radical containing about 2 to 10 carbon atoms.

14. The disposable garment of claim 1 wherein the polyhydrazide is selected from the group consisting of oxalyl dihydrazide, malonyl dihydrazide, succinyl dihydrazide, glutaryl dihydrazide, adipoyl dihydrazide, maleyl dihydrazide, sebacoyl dihydrazide, fumaroyl dihydrazide, isophthalic dihydrazide, terephthalic dihydrazide, and mixtures thereof.

15. The disposable garment of claim 1 wherein the polyhydrazide comprises about 0.5 to 150 milliequivalents per 100 grams of copolymer.

16. The disposable garment of claim 1 further comprising a multifunctional free-radically polymerizable crosslinking agent for internally crosslinking the microparticles.

17. The disposable garment of claim 1 wherein for the pressure-sensitive adhesive microparticles the sum of a)+b)+c) is 100 parts by weight; and the pressure-sensitive adhesive comprises about 0.5 to 150 milliequivalents per 100 grams of microparticles of said polyhydrazide crosslinking agent.

18. The disposable garment of claim 1 wherein for the pressure-sensitive adhesive microspheres:
monomer a) provides about 80 to 99 parts by weight;
monomer b) provides about 0.5 to 7 parts by weight;

monomer c) provides about 0 to 15 parts by weight.

19. The disposable garment of claim 18 wherein:

monomer a) provides about 85 to 98 parts by weight;

monomer b) provides about 1 to 5 parts by weight;

monomer c) provides about 0 to 10 parts by weight.

20. The disposable garment of claim 15 wherein the polyhydrazide crosslinking agent is present in an amount of about 1 to 100 milliequivalents.

21. The disposable garment of claim 20 wherein the polyhydrazide crosslinking agent is present in an amount of about 2 to 50 milliequivalents.

22. The disposable garment of claim 17 further comprising a crosslinking agent for internally crosslinking the microparticles.

* * * * *